United States Patent
Shelton, IV et al.

(10) Patent No.: US 10,765,426 B2
(45) Date of Patent: Sep. 8, 2020

(54) SYSTEMS FOR COUPLING ADJUNCTS TO AN END EFFECTOR

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US); David C. Yates, West Chester, OH (US); Prudence Vulhop, Cincinnati, OH (US); Susanne Landgrebe, Sufeld (DE); Marco Floris, Hamburg (DE)

(73) Assignee: Ethicon LLC, Guaynabo, PR (US)

( * ) Notice: Subject to any disclaimer, the term of this patent is extended or adjusted under 35 U.S.C. 154(b) by 645 days.

(21) Appl. No.: 15/436,328

(22) Filed: Feb. 17, 2017

(65) Prior Publication Data
US 2018/0235624 A1     Aug. 23, 2018

(51) Int. Cl.
*A61B 17/072*     (2006.01)
*A61B 17/00*      (2006.01)
*A61B 17/115*     (2006.01)

(52) U.S. Cl.
CPC .. *A61B 17/07207* (2013.01); *A61B 17/00491* (2013.01); *A61B 17/07292* (2013.01);
(Continued)

(58) Field of Classification Search
CPC ........ A61B 17/07207; A61B 17/00491; A61B 17/07292; A61B 17/1155;
(Continued)

(56) References Cited

U.S. PATENT DOCUMENTS

| | | | |
|---|---|---|---|
| 5,752,965 A | * | 5/1998 | Francis ............ A61B 17/07207 227/178.1 |
| 7,143,925 B2 | | 12/2006 | Shelton, IV et al. |

(Continued)

FOREIGN PATENT DOCUMENTS

| | | |
|---|---|---|
| EP | 2090252 A2 | 8/2009 |
| EP | 2764833 A2 | 8/2014 |
| EP | 3072457 A2 | 9/2016 |

OTHER PUBLICATIONS

Extended European Search Report for EP App. No. 18157230.6 dated Jun. 13, 2018 (14 pages).

*Primary Examiner* — Erich G Herbermann
(74) *Attorney, Agent, or Firm* — Mintz Levin Cohn Ferris Glovsky and Popeo, P.C.

(57) ABSTRACT

An adjunct loading system is provided that can include at least one adjunct material configured to be transferred from an adjunct loading member to first and second jaws of an end effector. The loading system can also include a supporting member configured to releasably retain the adjunct material. The loading system can further include an adhesive depot having an adhesive configured to transition from a non-flowable state to a flowable state upon application of heat when the adjunct material is released from the adjunct loading member and transferred to the jaw to retain the adjunct material on the jaw. The adjunct material is released from the adjunct loading member when load is applied thereto. The adhesive depot can be in the form of an adhesive feature formed on a polymer attachment layer or in the form of reservoirs in the supporting member.

12 Claims, 12 Drawing Sheets

(52) U.S. Cl.
CPC . *A61B 17/1155* (2013.01); *A61B 2017/00004* (2013.01); *A61B 2017/0046* (2013.01); *A61B 2017/00526* (2013.01); *A61B 2017/00951* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .. A61B 2017/00004; A61B 2017/0046; A61B 2017/00526; A61B 2017/00951; A61B 2017/07257; A61B 2017/07271; A61B 2017/07278; A61B 2017/07285
See application file for complete search history.

(56) References Cited

U.S. PATENT DOCUMENTS

| | | | |
|---|---|---|---|
| 7,601,118 B2 | 10/2009 | Smith et al. | |
| 8,317,070 B2 | 11/2012 | Hueil et al. | |
| 8,393,514 B2 | 3/2013 | Shelton, IV et al. | |
| 9,282,962 B2 | 3/2016 | Schmid et al. | |
| 2005/0070929 A1* | 3/2005 | Dalessandro | A61B 17/07207 606/151 |
| 2013/0214030 A1 | 8/2013 | Aronhalt et al. | |
| 2013/0221065 A1 | 8/2013 | Aronhalt et al. | |
| 2013/0256377 A1 | 10/2013 | Schmid et al. | |
| 2015/0076208 A1* | 3/2015 | Shelton, IV | A61B 17/068 227/176.1 |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351758 A1 | 12/2015 | Shelton, IV et al. | |
| 2016/0089142 A1 | 3/2016 | Harris et al. | |
| 2017/0055986 A1 | 3/2017 | Harris et al. | |

* cited by examiner

SYSTEMS FOR COUPLING ADJUNCTS TO AN END EFFECTOR

FIELD

The present disclosure relates generally to adjunct materials used in conjunction with an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

In some aspects, an adjunct loading system is provided that in some embodiments includes at least one adjunct material configured to be transferred from an adjunct loading member to first and second jaws of an end effector. The first and second jaws are configured to clamp tissue therebetween. The loading system also includes a supporting member configured to releasably retain the adjunct material. The loading system further includes an adhesive depot having an adhesive configured to transition from a non-flowable state to a flowable state upon the application of heat, when the adjunct material is released from the adjunct loading member and transferred to the jaw, to retain the adjunct material on the jaw.

The loading system can vary in many ways. For example, the adjunct material can be released from the adjunct loading member and transferred to one of the jaws under application of load to the adjunct loading member. The load can be applied to the adjunct loading member by the first and second jaws configured to clamp the adjunct loading member therebetween.

In some embodiments, the adhesive depot includes at least one protrusion formed on a polymer layer disposed on a jaw-facing surface of the adjunct material and comprising the adhesive. The adjunct material can be coupled to the polymer layer. In some embodiments, the at least one protrusion is formed at a location on the polymer layer corresponding to a location of an attachment feature formed on the jaw, the adhesive being configured to be disposed on the attachment feature. In some embodiments, the attachment feature includes a roughness pattern.

In some embodiments, the adhesive depot includes a plurality of reservoirs formed in the supporting layer and each releasably holding the adhesive. In some embodiments, the adhesive is held in the reservoirs in the non-flowable state in which the adhesive is substantially non-liquid such that the adhesive can transition under the application of at least one of heat and force to the flowable state in which the adhesive is at least partially liquid.

In some embodiments, the adhesive is held in the reservoirs in the non-flowable state in which the adhesive is substantially liquid such that the adhesive can transition under the application of at least one of heat and force to the flowable state in which the adhesive is at least partially non-liquid.

The adjunct material can include a plurality of openings, the openings being configured to receive the adhesive transitioning to the flowable state when the adhesive material is released from a respective one of the plurality of reservoirs and through the opening to a jaw-facing surface of the adjunct material to thereby retain the adjunct material on the jaw.

In some embodiments, the adhesive is caused to transition to the flowable state and is released from a respective one of the plurality of reservoirs under at least one of application of heat and application of load.

In at least some embodiments, the loading system includes at least one source of heat.

In other aspects, a surgical method is provided that in some embodiments includes positioning at least one adjunct loading member of a loading system releasably holding an adjunct material between first and second jaws of an end effector, the first and second jaws being configured to clamp tissue therebetween. The method also includes applying heat to at least a portion of an adhesive depot having an adhesive and disposed in the adjunct loading member in association with the adjunct material to cause the adhesive to transition from a non-flowable state to a flowable state when the adjunct material is released from the adjunct loading member and transferred to the jaw to retain the adjunct material on the jaw. The method further includes approximating the first and second jaws to thereby apply load to the adjunct loading member such that the adjunct material is transferred from the adjunct loading member to at least one of the first and second jaws.

The method can vary in many different ways. For example, in some implementations of the method, the adhesive depot includes at least one protrusion formed on a polymer layer disposed on a jaw-facing surface of the adjunct material and comprising the adhesive. The adjunct material can be coupled to the polymer layer.

In some implementations of the method, the at least one protrusion is formed at a location on the polymer layer corresponding to a location of an attachment feature formed on the jaw. In another implementation, the method further includes transferring the adjunct material to the jaw such that the adhesive of the at least one protrusion in the flowable state is disposed on the attachment feature.

In some implementations of the method, the adhesive depot includes a plurality of reservoirs each releasably holding the adhesive, the reservoirs being formed in a supporting layer of the adjunct loading member that has the adjunct material releasably disposed thereon. The adjunct material can include a plurality of openings. The adhesive transitioning from the non-flowable state to the flowable state can be released from a respective one of the plurality of reservoirs and through the opening to a jaw-facing surface of the adjunct material to thereby retain the adjunct material on the jaw

BRIEF DESCRIPTION OF THE DRAWINGS

The invention present disclosure will be more fully understood from the following detailed description taken in conjunction with the accompanying drawings, in which.

DETAILED DESCRIPTION

Figure 1:
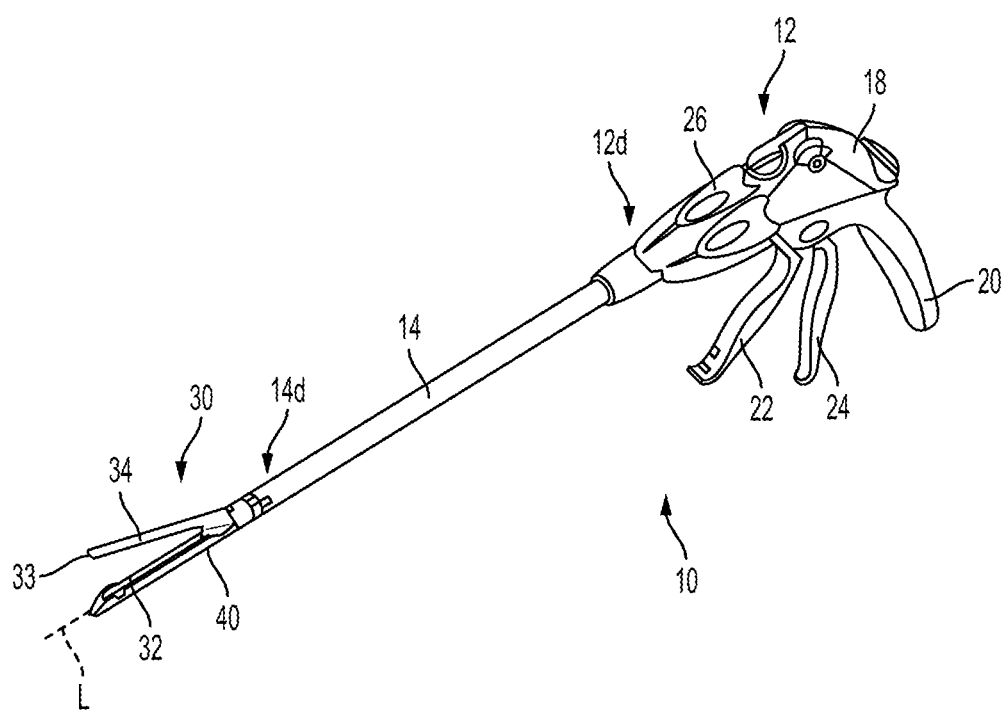
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example, linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
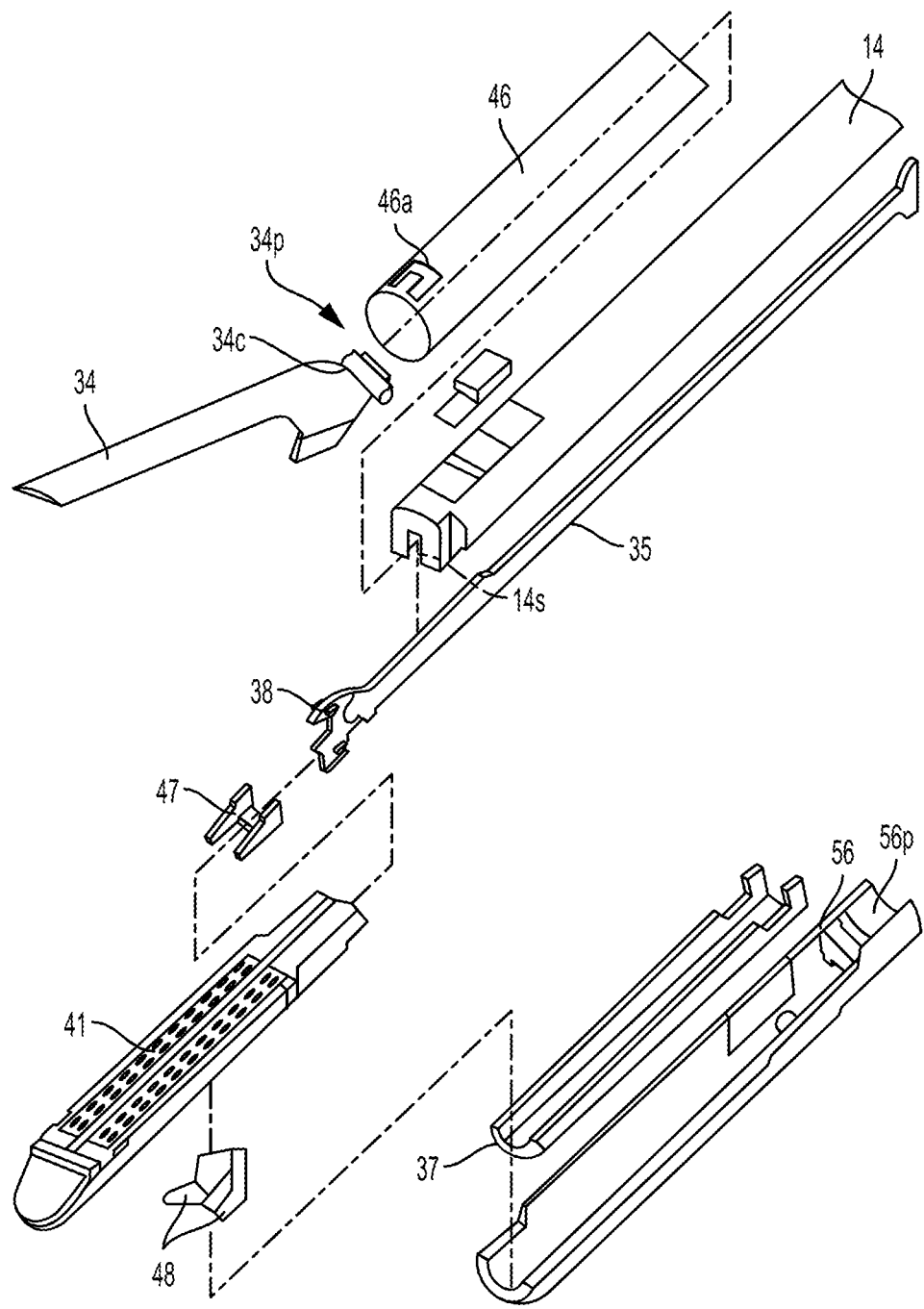
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
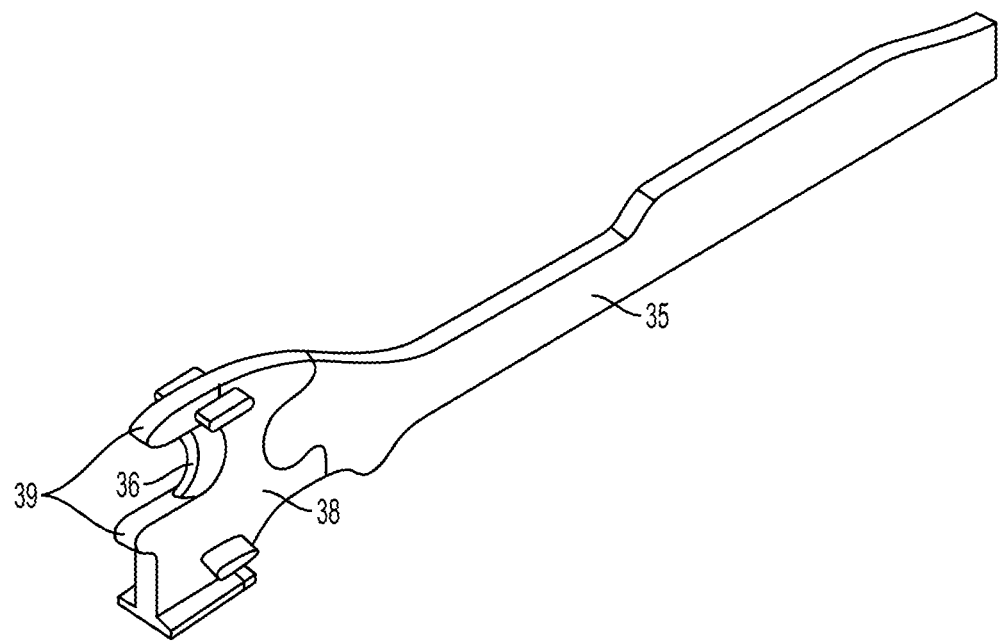
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
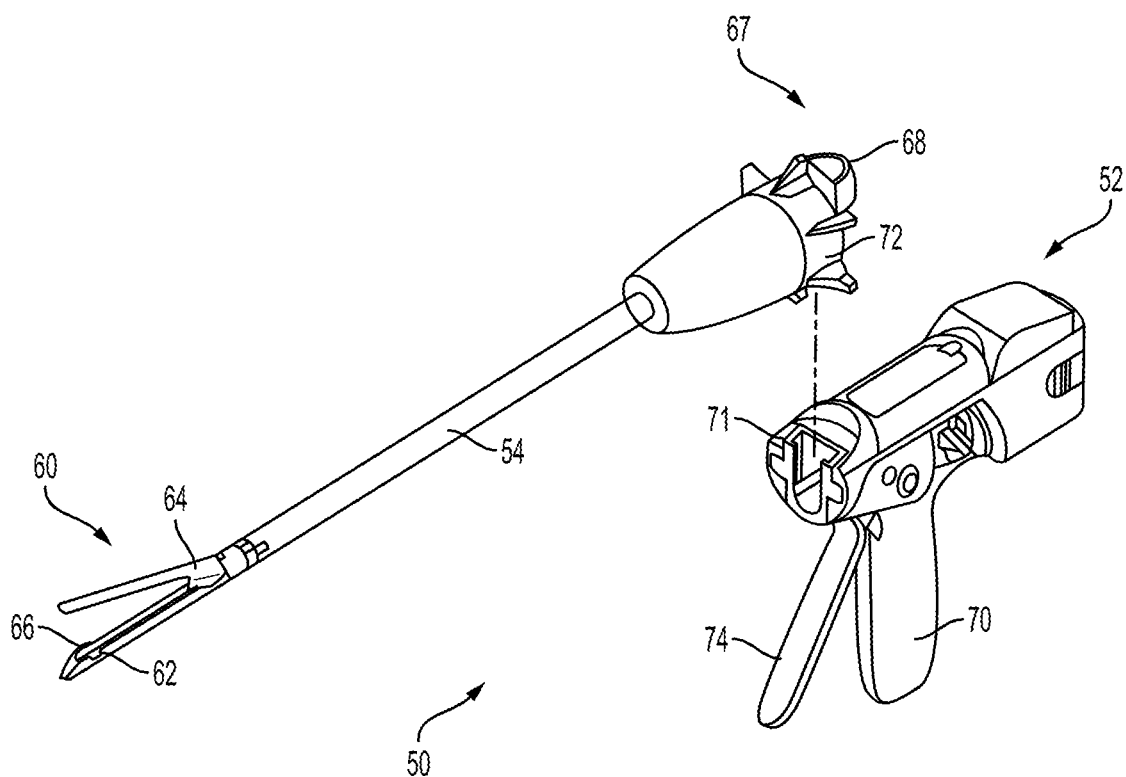
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
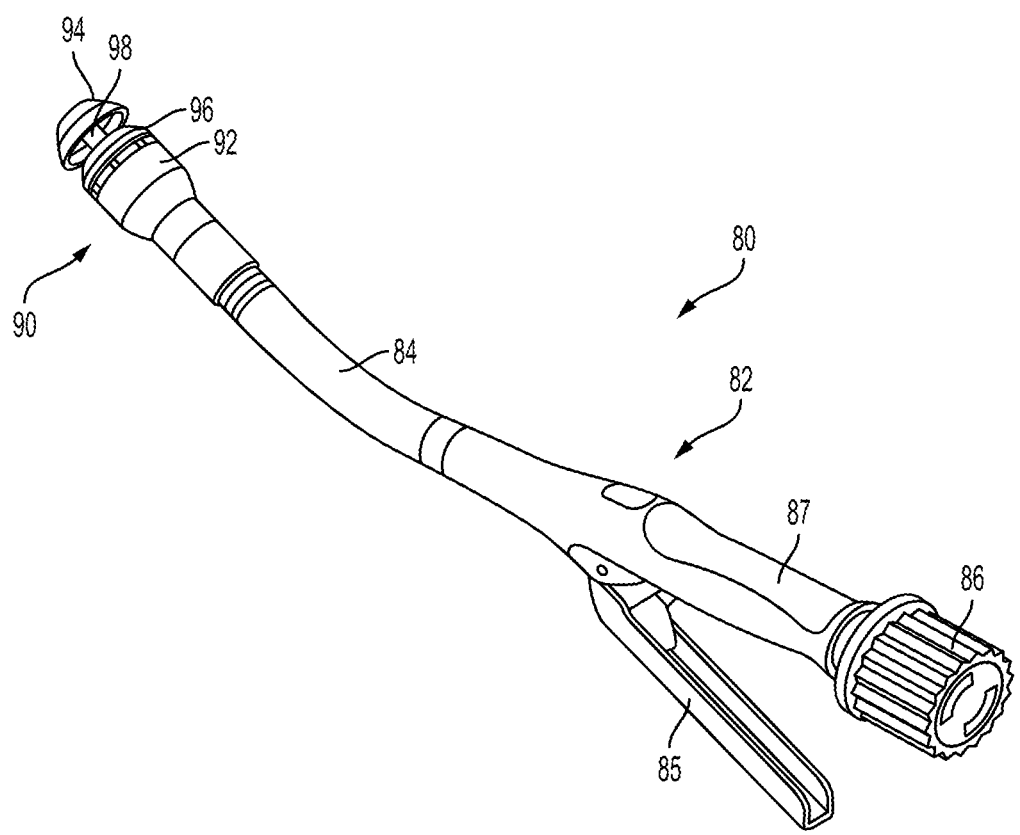
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam.

Examples of various foam adjuncts are further described in previously mentioned U.S. Pat. No. 8,393,514 entitled "Selectively Orientable Implantable Fastener Cartridge" and filed Sep. 30, 2010.

An adjunct can also be made from a film formed from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementation

Adjunct materials can be applied to one or both jaws of an end effector of a surgical instrument in various ways. For example, an adjunct material can be manually positioned on a jaw. It is desired to releasably couple an adjunct to a jaw such that the adjunct does not slip off the jaw prior to application of the adjunct to tissue when staples are fired. However, some approaches may not result in a secure enough attachment of the adjunct to a jaw. This compromises the ability of a surgeon to manipulate the surgical instrument with the adjunct as desired during the surgical procedure.

Accordingly, in some embodiments, systems and methods are provided for applying an adjunct material to a jaw of an end effector to be releasably retained thereon. The adjunct material can be coupled to the jaw using an adhesive that can be applied to the adjunct and/or the jaw in a controlled manner. In some implementations, the adjunct material can be coupled to the jaw via an intermediate polymer layer.

In some embodiments, an adjunct loading member of a loading system can be used that is configured to releasably hold at least one adjunct material. The adjunct material is configured to be transferred from the adjunct loading member to a jaw of first and second jaws of an end effector. A supporting member of a suitable configuration is configured to releasably retain the adjunct material that can be associated with the supporting member in various ways. For example, the adjunct material can be disposed on the supporting member. Additionally or alternatively, the supporting member can be in the form of retaining feature(s) releasably holding the adjunct material in the adjunct loading member. The adjunct loading member also includes an adhesive depot having an adhesive configured to transition from a non-flowable state to a flowable state upon the application of heat when the adjunct material is released from the adjunct loading member and transferred to the jaw. Once the adhesive in the flowable state is cooled, it adheres to the jaw and is thus used to retain the adjunct material on the jaw.

The adjunct material is configured to be released from the adjunct loading member under application of a load. The adjunct is transferred to the jaw and is caused to adhere to the jaw using the adhesive disposed in the adhesive depot when the adhesive is in the flowable state. Heat can be applied to the adhesive prior to or at least partially at the time when the adjunct is being released from the adjunct loading member to the jaw. The load can be applied by the jaws of the end effector when the adjunct loading member is clamped therebetween. Alternatively, the load can be applied to the adjunct loading member manually or in other ways. The application of at least one of load and heat causes the adhesive from the adhesive depot to be used to retain the adjunct material on the jaw of the end effector.

Figure 6:
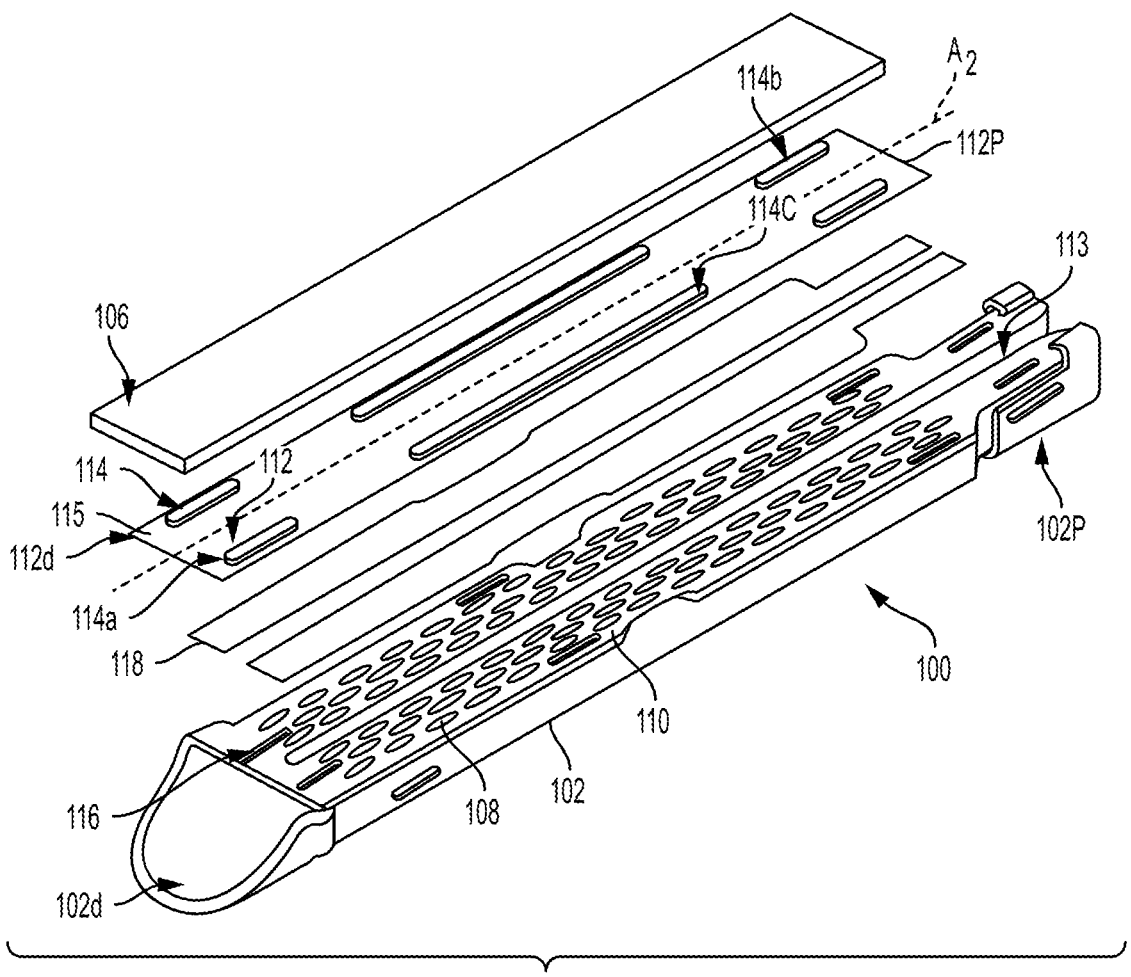
FIG. 6 is perspective, exploded view of a jaw of an end effector and an adjunct material configured to be coupled to the jaw via a polymer layer.

FIG. 6 illustrates an example of a portion an end effector 100 configured to releasably retain an adjunct material on one or both of its first and second opposed jaws configured to clamp tissue therebetween, in accordance with the described techniques. The end effector 100, partially illustrated in FIG. 6, has a first jaw having a cartridge body or cartridge 102 and a second jaw having an anvil (not shown), with the first and second jaws being configured to clamp tissue therebetween. The cartridge body 102 is configured to releasably retain thereon an implantable adjunct material 106. The end effector 100 can be coupled to a distal end of a shaft of the surgical instrument (not shown). The end effector 100 can be used in any suitable surgical instrument, for example, a linear surgical stapler (e.g., stapler 10 in FIG. 1, stapler 50 in FIG. 4, or any other surgical stapler, including a circular stapler, such as stapler 80 in FIG. 5) which can be suitable for use with at least one adjunct.

As shown in FIG. 6, the cartridge body 102 has a plurality of staple or staple-holding cavities 108 configured to seat staples therein, the staple-holding cavities 108 opening on a tissue-facing surface 110 of the cartridge 102. The staple cavities 108 form a certain pattern on the surface of the cartridge 102 which corresponds to a pattern of staple-forming cavities formed in the anvil (not shown). The cartridge 102 includes a cutting element or knife channel 113 extending between distal and proximal ends 102d, 102p of the cartridge 102. The knife channel 113 is configured to receive a cutting element (e.g., a knife) as it moves distally therethrough. As shown in FIG. 6, the staple cavities 108 can form three rows on both sides of the cutting element channel 113, though it should be appreciated that the staple cavities 108 can form any other patterns on the tissue-facing surface 110.

The cartridge body 102 can be in the form of a staple channel configured to support a staple cartridge, which can be removably and replaceably seated within the staple channel. Furthermore, in some embodiments, the cartridge 102 can be part of a disposable loading unit coupled distally to a shaft of a surgical instrument.

In this example, the end effector 100 is configured to releasably retain thereon the implantable adjunct material (or "adjunct") 106. In the illustrated implementation, the adjunct material 106 releasably retained on the cartridge 102 is discussed, though it should be appreciated that the anvil can also have an adjunct material releasably retained thereon. The adjunct material 106 can be applied to the cartridge 102 using a loading member of a loading system, such as an adjunct loading member 200 shown in FIG. 8 and discussed in detail below.

Figure 7:
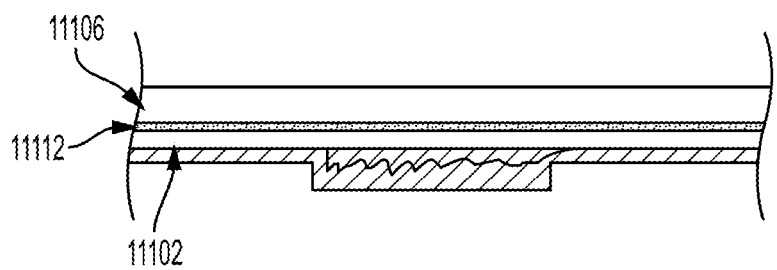
FIG. 7 is a cross-sectional view of a portion of the adjunct material of FIG. 6 coupled to the jaw of the end effector via the polymer layer.

Regardless of the configuration of the loading member, the adjunct material 106 is configured to be transferred from the loading member to the cartridge 102 using an adhesive depot having an adhesive configured to transition from a non-flowable state to a flowable state upon the application of heat when the adjunct material is released from the adjunct loading member and transferred to the jaw to retain the adjunct material on the jaw. The adhesive depot can have a variety of configurations and it can be configured to allow the adhesive to be released therefrom in a variety of ways. In this example, as shown in FIG. 6, the adhesive depot is in the form of protrusions formed on a polymer attachment layer or polymer layer 112 disposed on a jaw-facing surface of the adjunct material 106, as also shown schematically in FIG. 7. In particular, the polymer layer 112, shown in FIG. 6 with its jaw-facing surface 115 facing up for the illustration purposes only, has a plurality of protrusions 114 including or formed from an adhesive. In FIG. 6, the polymer layer 112 has two shorter protrusions (collectively referred to as 114a, 114b) at each of distal and proximal ends 112d, 112p thereof, respectively, and two longer protrusions 114c disposed between the protrusions 114a, 114b. The pairs of protrusions 114a, 114b, 114c are formed along a longitudinal axis A2 of the polymer layer 112, and symmetrically with respect to a centerline of the polymer layer 112.

As shown in FIG. 6, the tissue-facing surface 110 of the cartridge 102 can include attachment features 116 configured to engage the protrusions 114. In particular, the adhesive included in the protrusions 114 or from which the protrusions 114 are formed can be disposed on the attachment features 116. The attachment features 116 can have various configurations. For example, they can be formed as recesses in the cartridge 102. Additionally or alternatively, the attachment features 116 can include a roughness pattern, which can be formed in any suitable manner. The roughness pattern can have any suitable texture. For example, in one embodiment, the attachment features 116 can be formed by making grooves having a pattern of multiple "Xs" (or other shapes or features) on the surface of the jaw. In this example, the cartridge 102 is shown to have six attachment features formed at the distal and proximal ends 102d, 102p thereof, symmetrically with respect to the channel 113. It should be appreciated however that a cartridge of an end effector can include any other number of the attachment features (e.g., less then eight or greater than eight).

The protrusions 114 formed on the polymer layer 112 and the attachment features 116 formed on (or in) the cartridge 102 can have various shapes, including different shapes. For example, they can be generally elongate and rectangular, as shown in FIG. 6. Additionally or alternatively, they can be square, semi-circular (e.g., having a semi-circular or oval shape as viewed from the top), and/or they can have any other suitable regular or irregular shapes.

In some embodiments, at least one protrusion can be formed at a location on the polymer layer corresponding to a location of an attachment feature formed on the jaw. Thus, as shown in FIG. 6, the six protrusions 114 are formed on the polymer layer 112 at locations that correspond to the locations of the six attachment features 116. The length and width of the protrusions 114 can be different from those of the attachment features 116. In addition, in some cases, one protrusion can be disposed over more than one attachment feature, and vise versa. Thus, the protrusions formed on the polymer layer and the attachment features formed on the jaw can form various patterns and can correspond to one another in various manners.

Regardless of the specific number, size, and locations of adhesive protrusions formed on the polymer layer 112, the polymer layer 112 is used to attach the adjunct material 106 to the cartridge 102. The surface of the polymer layer 112 that is opposed to the surface 115 on which the protrusions 114 are formed can be coupled to the adjunct material 106 in various ways. For example, at least a portion of the polymer layer 112 can be formed from a pressure-sensitive adhesive such that the adjunct material 106 can be coupled with the polymer layer 112 that is, in turn, coupled with the jaw.

In some embodiments, as shown in FIG. 6, the end effector 100 can include an additional polymer layer 118 shown in the form of two portions. The additional polymer layer 118 can be disposed between the adjunct material 106 and the polymer layer 112 or between the polymer layer 112 and the cartridge 102. The additional polymer layer 118 can be formed from an adhesive configured to transition from a non-flowable state to a flowable state upon the application of heat. Thus, when the additional polymer layer 118 is configured to be disposed between the polymer layer 112 and the cartridge 102, it is effectively additionally used to couple the adjunct material 106 to the jaw 102. It should be appreciated however that the additional polymer layer 118 is optional and may not be present.

The adjunct material 106 can be formed from any suitable material or a combination of materials, which are discussed above. In some embodiments, the adjunct material 106 can have a thickness of from about 0.006 inches to about 0.008 inches. In some embodiments, the adjunct material 106 can have a thickness of from about 0.004 inches to about 0.0160 inches. The polymer layer can have a thickness of from about 0.002 inches to about 0.025 inches, and projections 116*d*, 116*p* can have a height or thickness of from about 0.005 inches to about 0.025 inches.

Figure 8:
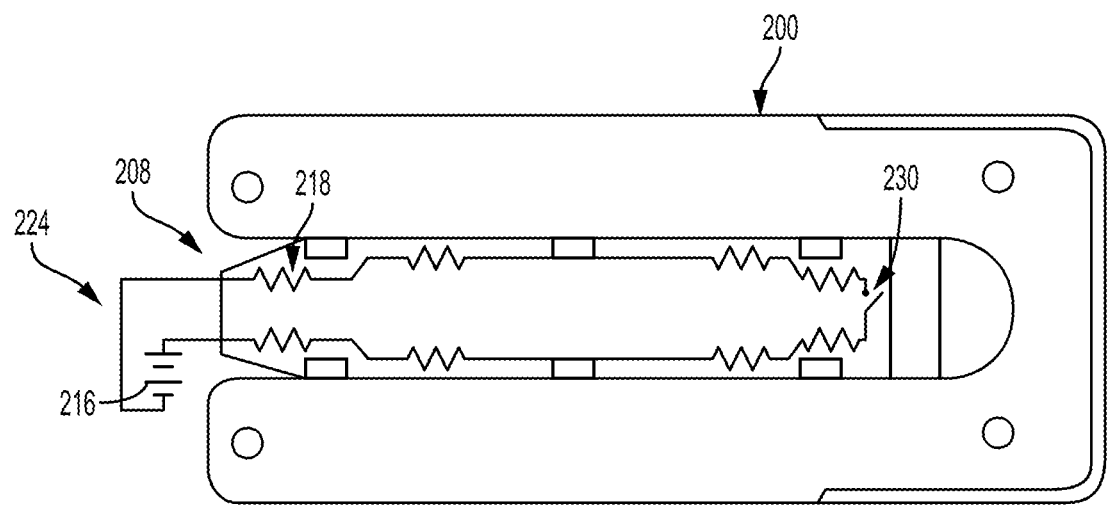
FIG. 8 is a top view of an adjunct loading member.
Figure 9:
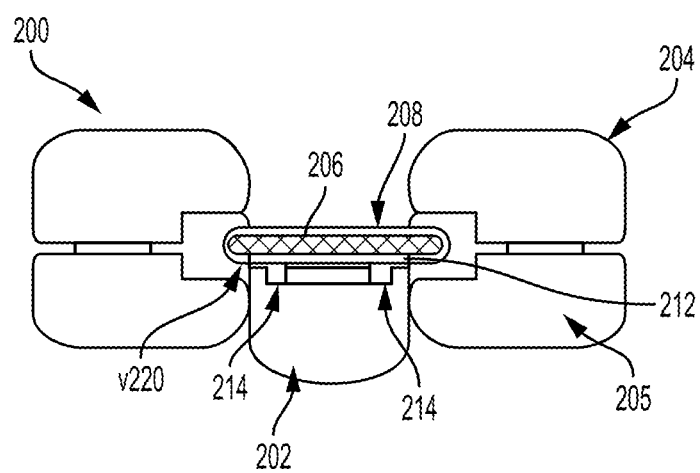
FIG. 9 is a cross-sectional view of the adjunct loading member of FIG. 8.

As mentioned above, in the described embodiments, the adjunct material is configured to be transferred from an adjunct loading member to a jaw of an end effector. FIGS. 8 and 9 show an example of an adjunct loading member 200 of a loading system that is configured to release the adjunct material to retain the adjunct material in the jaw, using at least one of heat and load (force). FIG. 8 shows a top view of the adjunct loading member 200, whereas FIG. 9 shows a cross-sectional view of the adjunct loading member 200 when it is disposed on a jaw 202 of an end effector.

As in the illustrated example, the adjunct loading member 200 can be the form of a generally rectangular frame-like holder configured to releasably couple one or more adjuncts to one or both jaws of the end effector (not shown in FIGS. 8 and 9). In the illustrated example, the adjunct loading member 200 is in the form of a first (e.g., top) and second (e.g., bottom) generally rectangular housings 204, 205 coupled to one another e.g., via a coupling member. In this example, the adjunct loading member 200 can be used to apply a single adjunct to a jaw. It should be appreciated however, that, in some embodiments, a loader like the adjunct loading member 200 or a similar loader, can be used to apply a respective adjunct to each jaw of an end effector.

As shown in FIG. 8, the adjunct loading member 200 includes at least one heating component 208 configured to be activated to apply heat to an adhesive depot having an adhesive configured to transition from a non-flowable state to adhering flowable state upon the application of heat. In this example, as shown in FIG. 9, the adjunct loading member 200 can retain thereon an adjunct material 206 and a polymer layer 212 having protrusions 214. The adjunct material 206 and the polymer layer 212 can be similar, for example, to the adjunct material 106 and the polymer layer 112, though any suitable number of the protrusions 214 can be formed on the polymer layer 212.

As shown in FIG. 8, the adjunct material 206 can be releasably retained on a supporting member 220 that can be configured in any suitable manner so as to retain the adjunct material 206. The supporting member 220 that can have or can be in the form of, for example, retaining features (not shown) configured to releasably hold the adjunct material 206. The adjunct material 206 can be disposed in any suitable way with respect to the supporting member. For example, in some embodiments, the supporting member 220 can be in the form of features formed on one or more sides of the adjunct material 206. In this way, when load is applied to the adjunct loading member 200, the supporting member 220 is caused to release the adjunct material 206 therefrom, thus causing the adjunct material to be transferred to a jaw of an end effector. FIG. 9 illustrates by way of example a jaw of an end effector in the form of a cartridge 202 that has the adjunct loading member 200 associated wherewith. The cartridge 202 is shown in FIG. 9 to have the adjunct material 206 transferred thereto and coupled thereto using the polymer layer 212. It should be appreciated that, although not shown in FIG. 9, in use, the load is applied to the adjunct loading member 200 by a first jaw having an anvil and the second jaw having cartridge 202 that are clamped together with the adjunct loading member 200 disposed therebetween.

In the described embodiments, the adjunct material 206 is transferred from the adjunct loading member 200 to the cartridge 202 under application of load and the adjunct material 206 is caused to be retained on the cartridge 202 using an adhesive that is caused to transition to a flowable state under application of heat. Thus, in use, the adjunct loading member 200 releasably holding the adjunct material 206 is positioned between the jaws of the end effector (only the cartridge 202 of the end effector is shown in FIG. 9). To transfer the adjunct material 206 from the adjunct loading member 200 to the jaw 202, the first and second jaws are approximated to thereby apply load to the adjunct loading member 202, which causes the adjunct material 206 to be released from the adjunct loading member 200. The adjunct loading member 200 can be configured such that it exposes the side of the polymer layer 212 (having the adjunct 206 coupled thereto) having the protrusions 214. The application of load can cause the supporting member 220 and, in some implementations, other portions or features of the adjunct loading member 200 to crack, break, deform (e.g., bend, flex, etc.) or otherwise change their configuration to thereby release the adjunct 206 from the adjunct loading member 200. In some embodiments, the housings 204, 205 of the adjunct loading member 200 can be configured to deform or break to release the adjunct 206 from the adjunct loading member 200 when the adjunct loading member 200 is clamped between the jaws 200 (and not shown) of the end effector such that the load is applied thereto. As such, the adjunct 206 can be "squeezed out" of the adjunct loading member 200. The adjunct loading member 200 can be disposable such that it can be discarded after the adjunct 206 (and the polymer layer 212 coupled thereto) is transferred to the jaw.

Heat is applied to at least a portion of an adhesive depot such as the protrusions 214 of the polymer layer 212 having an adhesive and disposed in the adjunct loading member 200 in association with the adjunct material 206, which causes the adhesive to transition from a non-flowable state to adhering flowable state when the adjunct material 206 is released from the adjunct loading member 200 and transferred to the jaw 202. For example, under the application of heat, the adhesive from which the protrusions 214 are formed can transition from a substantially non-liquid state (in which it is in the non-flowable state) to at least partially liquid state (in which the adhesive is in the flowable state). In the at least partially liquid state, the protrusions 214 can become less viscous such that their material can flow and interconnect or adhere with the surface of the cartridge 202. The cartridge 202 can have attachment features (e.g., similar to the attachment features 116 in FIG. 6) that can have the protrusions 214 in the flowable state disposed thereon such that the protrusions 214 on the polymer layer 212 adhere to the surface of the cartridge 202. Because the polymer layer 212 is coupled to the adjunct material 206, adhering the polymer layer's protrusions 214 to the cartridge 202 causes the adjunct material 206 to be releasably retained on the jaw 202. When the material from which the protrusions 214 are formed is cooled and thus transitions to the flowable state, the protrusions 214 remain attached to the cartridge 202.

In some embodiments, the adjunct loading member 200 can be activated (e.g., using a button, switch, or other suitable trigger on the member 200 or a remote trigger), to apply heat to the polymer layer 212 before (or as) the load is applied to the adjunct loading member 200. For example, the heating component 208 can be activated before the adjunct loading member 200 is positioned between the jaws of the end effector. The adjunct loading member 200 can be configured to deliver to the polymer layer 212 heat of a desired temperature (e.g., in a range of from about 105° C. to about 220° C.) for an appropriate duration of time (e.g., from about 5 seconds to about 60 seconds) such that the application of heat causes the protrusions 214 of the polymer layer 212 to transition from the non-flowable state to the flowable, deformable state. In some embodiments, an indicator configured to indicate that the adhesive has been sufficiently heated to the deformable state can be activated. This can be, for example, a light indicator, an audio indicator, etc.

Once the protrusions 214 are in the flowable state, the adjunct loading member 200 can be disposed between the approximated jaws that cause the protrusions 214, and thus the adjunct 206 coupled thereto, to attach to the jaw 202. Furthermore, in some embodiments, heat can be applied once the adjunct loading member 200 is disposed between the jaws but prior to the jaws applying the load to the adjunct loading member 200. As another variation, the adjunct loading member 200 can be activated to apply heat to at least a portion of the polymer layer 212 and adjunct 206 at least partially simultaneously with the load being applied to the adjunct loading member 200.

Regardless of the specific timing of the application of load and heat to the adjunct 206 and polymer layer 212, the adhesive of the protrusions 214 is caused to transition to the flowable state in which the protrusions 214 attach to the jaw 202 thus causing, after the heat is no longer applied, the polymer layer 212 to be attached to the jaw. The application of at least one of the load and heat can also cause the adjunct 206 to couple to the polymer layer 212.

The heating component 208 can have various configurations. For example, as shown in FIG. 8, the heating component 208 includes a resistive heating element 224 in the form of a wire, which is connected to a power source 216. In the illustrated example, as shown, the heating element 224 includes higher resistance portions 218 along its length. The locations of the higher resistance portions 218 can correspond to regions on the polymer layer to which heat is desired to be applied, e.g. regions having the protrusions 114 (FIG. 6). Thus, power can be applied to the heating element 224 to cause localized heating near the higher resistance portions 218. In this way, the heat is applied selectively to the polymer layer and to the adjunct material coupled thereto.

In some embodiments the heating element 224 can include a switch 230 configured to close the circuit and to allow current to flow through the heating element. The switch 230 can be operated using a suitable trigger associated with the adjunct loading member 200 (e.g., a button or other switch on the loader 200 activated by closure of the end effector or by the person loading the device or a remote control), though the heating element 224 can be activated in other suitable ways. The heat generated by the higher resistance portions 218 causes the adhesive portions of the polymer layer, such as the protrusions, to transition to the flowable state and thus couple the polymer layer and the adjunct coupled thereto to the jaw when the polymer layer and adjunct are transferred to the jaw.

The heating component 208 can be of any suitable type. For example, the heating component 208 can be made of a rigid material, e.g., ceramic, that is coated with an elastic or compliant material. In some embodiments, the heating component 208 can be in the form of a resistive wire embedded into silicone, e.g., such that the silicone is cured around the resistive wire. The resistive wire is configured to effect the heating, whereas the silicone allows for some degree of compliance when clamping a stapler onto the loader. The heating component 208 can be coupled to the housings 204, 205 in any suitable manner, e.g., via brackets.

As mentioned above, the adjunct loading member 200 is generally be configured such that the adjunct 206 is releasably retained in association therewith adjunct loading member 200 using a supporting member 220. The supporting member 220 can be in the form of a surface and/or it can include retaining features that can releasably couple the adjunct 206 and the polymer layer 212 to the adjunct loading member 200. The adjunct 206 can be disposed on the heating component 208, as shown schematically by way of example only in FIG. 9. In this way, once the heating component 208 is activated, heat is applied to the adjunct 206 and the polymer layer 212 that faces the jaw 202.

In some embodiments, an adjunct loading member, which can be similar to the adjunct loading member 200 can be configured to releasably retain first and second adjuncts, each configured to be transferred to a respective one of first and second jaws of an end effector. The adjuncts can be secured to both jaws of the end effector simultaneously. A heating component can be configured to apply heat to polymer layer's protrusions or other adhesive depots associated with the adjuncts to retain the adjuncts on the respective jaws. Furthermore, in some embodiments, the heating component can be in the form of two heating components disposed in the removable loader such that each of the heating components is configured to apply heat to a different adjunct that can be associated therewith (e.g., via the loader or manually).

After the adjunct 206 is coupled to the jaw 202 and the heat is no longer applied thereto, the adhesive from which the protrusions 214 are formed can at least partially return to the original state, although not to the original shape. This can occur because the heat source is removed (i.e. the adjunct loading member 200 is removed, or the power to the heaters is switched off after a set time) and the adhesive is exposed to a room temperature. This can be done while the polymer layer 212 remains at least partially associated with the adjunct loading member 200. Also, the adjunct loading member 200 can be part of a loading system including other components, and such loading system can be configured to cool the adhesive coupling the polymer layer 212 to the jaw. For example, a cool air can be applied to the polymer layer 212 coupled to the adjunct 206. In some embodiments, the cooling can be done using a separate component.

In some embodiments, a trigger associated with the loader (e.g., a switch) is configured to be activated to turn on the heating components once the end effector is clamped onto the loader. This causes the resistors to be heated which thus cause the polymer layer to be heated. The compression or load from the end effector causes the adhesive to flow and conform to the features on the jaw. The power to the resistors can automatically cease after a preset time (either a timer in the circuit, or the circuit can self-destruct with time/heat, or the battery can expire, etc.). After the heat is no longer applied, the polymer adhesive will cool, e.g., due to the thermal mass of the jaws. The loader, or other suitable component, can be configured to, after a time sufficient for the adhesive to cool and thus transition to an adhered state has passed, provide an indication indicating that the process of adhering the adhesive (and thus coupling the adjunct to the jaw) has been completed. The indication can be provided in any suitable way—for example, it can be a visual (e.g., light) indicator, audio indicator, any combination of a visual/audio indicator, etc.

Regardless of the manner in which the adhesive coupling the polymer layer 212 to the jaw 202 is cooled, the adhesive at least partially hardens or solidifies. The adjunct 206 is coupled to the jaw 202 via the polymer layer 212 with the protrusions 214 in a releasable manner and can thus be separated from the jaw 202. For example, when staples are fired from the jaw 202, the bond between the adhesive and the jaw 202 can break or crack.

The polymer layer 212 and the protrusions 214 formed thereon can be made from any suitable material or a combination of materials. Also, they can be bioabsorbable and/or biodegradable. The protrusions 214 can be formed from a material having a lower melting point than a melting point of a material from which the polymer layer 212 is made. For example, if the material from which the protrusions 214 are made is PDO, its melting point can be less than about 105° C. However, materials with a melting point that is less than about 180° C. can be used additionally or alternatively. When heat is applied to the polymer layer 212 (e.g., selectively, such that portion(s) of the protrusions are exposed to heat), the adhesive of the protrusions 214 can be transitioned to a flowable state, whereas the state of an adhesive from which the polymer layer 212 is made does not change.

In some embodiments, an adhesive depot having an adhesive configured to transition from a non-flowable state to a flowable state upon the application of heat is in the form of a plurality of reservoirs. The plurality of reservoirs can be formed in a supporting layer of an adjunct loading member and each can releasably hold the adhesive.

Figure 10A:
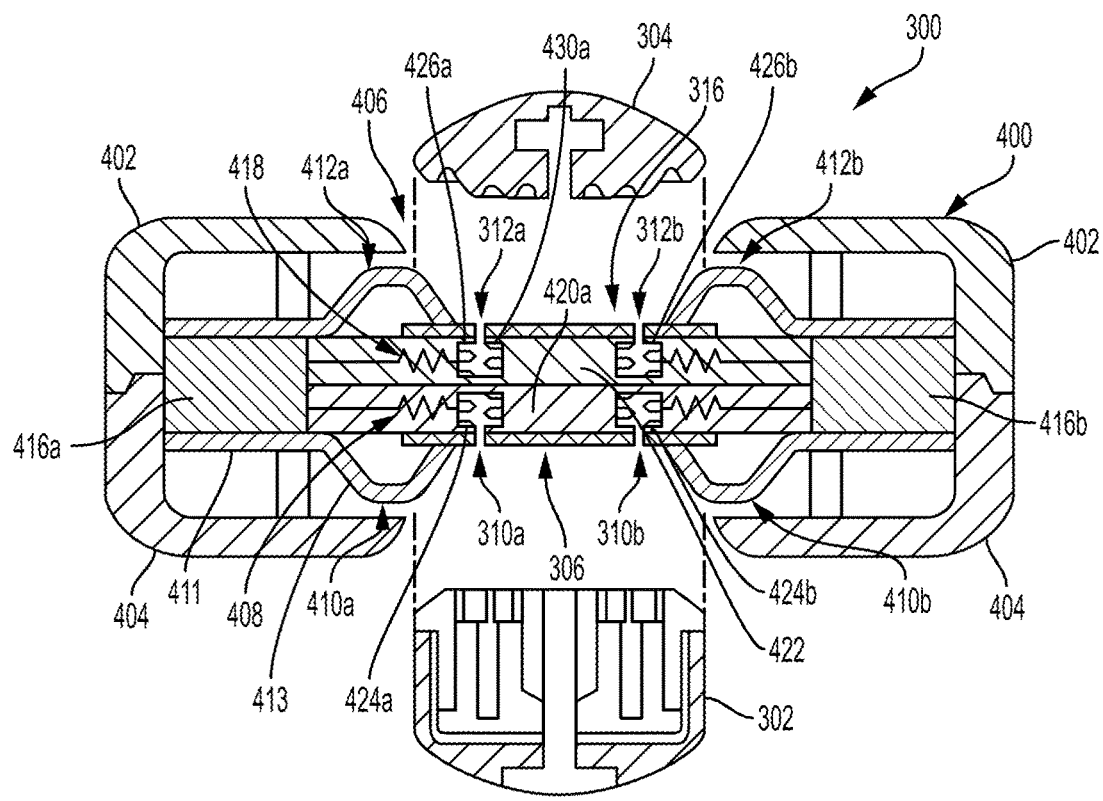
FIG. 10A is a cross-sectional view of an adjunct loading member configured to apply an adjunct material to first and second jaws of an end effector.
Figure 10B:
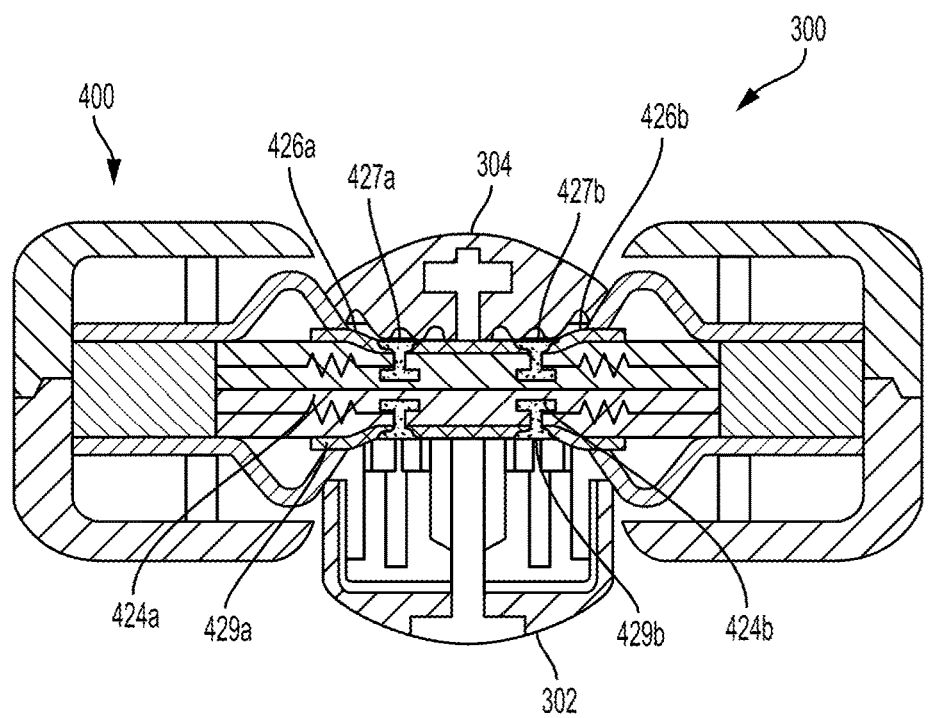
FIG. 10B is a cross-sectional view of the adjunct loading member of FIG. 10A, illustrating the adjunct material applied to the first and second jaws of the end effector.

FIGS. 10A and 10B illustrate an embodiment of an adjunct loading member 400 releasably holding first and second adjunct materials 306, 316 on first and second supporting members 420, 422, respectively. The adjunct loading member 400 is used to transfer the first and second adjunct materials 306, 316 to first and second jaws 302, 304 of an end effector 300, as discussed below. In this example, the first jaw 302 has a cartridge (which can be removably and replaceably seated in the jaw or which can be part of a reloadable unit including the first jaw 302 or both the first and second jaws 302, 304), and the second jaw 304 has an anvil.

In the illustrated embodiment, the adjunct loading member 400 is in the form of a generally rectangular member having first and second generally rectangular housings 402, 404 coupled to one another. As shown, the adjunct loading member 400 includes an adjunct holding member 406 extending between the housings 402, 404 and including various components. In particular, the adjunct holding member 406 includes body members 416a, 416b shown in the left and right sides of the adjunct loading member 400, respectively, brackets 410a, 412a at one side of the adjunct loading member 400 (left in FIGS. 10A and 10B), brackets 410b, 412b at another side of the adjunct loading member 400 (right in FIGS. 10A and 10B), and the first and second supporting members 420, 422 extending between the body members 416a, 416b.

The supporting members 420, 422 are disposed in the adjunct loading member 400 such that their mid-portions having the first and second adjunct materials 306, 316 releasably retained thereon are not encompassed by the housings 402, 404. The brackets 410a, 410b extend over the body members 416a, 416b at one side thereof (bottom in FIGS. 10A and 10B) and retain the first adjunct 306 over the supporting member 420. In a similar manner, the brackets 412a, 412b extend over the body members 416a, 416b at another, opposed side thereof (top in FIGS. 10A and 10B) and retain the second adjunct 316 over the supporting member 422.

As shown, each of the brackets has a straight portion (e.g., a portion 411 of the bracket 410a) extending along and over one of the body members 416a, 416b, and a trapezoid-shaped deformable portion (e.g., a portion 413 of the bracket 410a) extending from the straight portion towards a center of the adjunct loading member 400. One end of each of the trapezoid-shaped deformable portion of the brackets 410a, 410b, and 412a, 412a is disposed over the first and second adjunct materials 306, 316, respectively. It should be appreciated that the brackets are shown to have the trapezoid-shaped deformable portion by way of example only, as the brackets can have any other configuration.

In the illustrated embodiments, the adhesive depots are in the form of reservoirs formed in the supporting members. Thus, as shown in FIG. 10A, the supporting member 420 has reservoirs 424a, 424b, and the supporting member 422 has reservoirs 426a, 426b. Each of the reservoirs 424a, 424b, 426a, 426b releasably holds an adhesive and includes an opening through which the adhesive can be released from that reservoir. For example, in FIG. 10, the reservoir 426a is shown to have an opening 430a, and other reservoirs have similar openings. As also shown, each of the adjunct materials 306, 316 includes a plurality of openings each having a reservoir with adhesive associated therewith. In particular, the adjunct material 306 has openings 310a, 310b disposed adjacent to the openings in the reservoirs 424a, 424b. Similarly, the adjunct material 316 has openings 312a, 312b disposed adjacent to the openings in the reservoirs 426a, 426b. It should be appreciated, however, that in some embodiments, the reservoirs can be configured differently—e.g., they may not have openings, but can have a breakable, meltable, or otherwise removable enclosure that allows to retain the adhesive in the reservoirs and that can be removed when it is desired to release the adhesive. Additionally or alternatively, openings configured to allow an adhesive to flow from the reservoir can be formed in the supporting member.

The openings, such as the openings 310a, 310b in the adjunct material 306 and the openings 312a, 312b in the adjunct material 316, are formed at locations in the adjuncts at which it is desired to form attachment portions or points (made of an adhesive) that couple the adjuncts to the jaw. The opening locations in each of the adjuncts can be selected so as to facilitate attachment of the adjunct to the jaw and to also facilitate release of the adjunct from the jaw. It should be appreciated that the adjuncts 306, 316, which are shown in FIGS. 10A and 10B in cross-section, can include more than two openings. Multiple openings can be formed so as to attach the adjunct to the jaw using an adhesive at more than two locations. For example, four, six, eight, or more openings can be formed in each of the adjuncts. Also, although, as in the example in FIGS. 10A and 10B, the openings can be formed in pairs (e.g., they can be disposed symmetrically along a centerline of the adjunct), an odd number (e.g., three, five, etc.) of openings can be formed, which corresponds to an odd number of attachment points to be formed when the adjunct is coupled to the jaw.

The adjunct loading member 400 has first and second heating components 408, 418 extending through the supporting members 420, 422 that are configured to apply heat to the adhesive held in the reservoirs 424a, 424b and 426a, 426b, respectively, to cause the adhesive to transition from a non-flowable state to a flowable state. In some implementations, a single heating component can be used. Also, the first and second heating components 408, 418 can be parts of the same heating component. The openings 310a, 310b, 312a, 312b are configured to receive the adhesive transitioning to the flowable state when the adhesive material is released from a respective one of the reservoirs and through the opening to a jaw-facing surface of the respective adjunct material to thereby retain that adjunct material on the jaw.

In use, the adjunct loading member 400 having the adjunct materials 306, 316 releasably retained thereon is disposed between the first and second jaws 302, 304 of the end effector 300, as shown in FIG. 10A that illustrates the adjunct loading member 400 before a load is applied thereto. The load is then applied to the adjunct loading member 400 by the first and second jaws 302, 304 that clamp the adjunct loading member 400 therebetween, as shown in FIG. 10B. Under the application of load exerted by the jaws, the adjunct loading member 400 is at least partially deformed, which causes the adjunct materials 306, 316 to be transferred to the jaws 306, 316, respectively. For example, the brackets 410a, 410b, and the brackets 412a, 412a can be at least partially deformed. Also, the supporting members 420, 422, which can be formed from a silicone or other deformable and resilient material(s), are deformed under the load, as shown in FIG. 10B. When load is applied to the adjunct loading member 400, the supporting members 420, 422 apply pressure to the adjunct materials 306, 316, which can be done in the manner that facilitates uniform application of the load to the adjunct materials. This helps apply the adjunct to the jaws in a uniform manner.

In the illustrated example, the adjunct loading member 400 is configured so that the adjunct materials 306, 316 are transferred substantially simultaneously to the jaws 306, 316. It should be appreciated, however, that in some embodiments the adjunct loading member can be configured to transfer one adjunct to an end effector's jaw.

Before or at the time when the load is applied to the adjunct loading member 400, the heating components 408, 418 are activated to cause heat to be applied to the reservoirs 424a, 424b and 426a, 426b, respectively, to cause the adhesive in the reservoirs to transition from the non-flowable state to the flowable state. The adhesive can be stored in the reservoirs 424a, 424b, 426a, 426b in a substantially non-liquid state, and, under the application of heat, the adhesive can become at least partially liquid such that it can be used to couple the adjunct materials to the jaws. As shown in FIG. 10B, when the load is applied, the adhesive is released from the reservoirs, through the openings in the adjuncts 306, 316, and onto the surface of the jaws 302, 304. In this way, the portions of adhesive 427a, 427b and 429a, 429b released from the reservoirs 424a, 424b and 426a, 426b, respectively, are used to retain the adjunct materials on the opposed jaws of the end effector 300.

The reservoirs 424a, 424b, 426a, 426b can have any suitable configurations and they can be configured to release the adhesive stored therein in various ways. In the illustrated example, they are at least partially enclosed structures that store the adhesive. For example, they can be formed from a rigid plastic having a liquid adhesive (e.g., a pressure-sensitive adhesive) stored therein. As mentioned above, the reservoirs can have openings formed on the side thereof adjacent to the adjunct.

Furthermore, in some embodiments, the adjunct loading member 400 can include a closure component that can be disposed so as to temporarily enclose one side of the reservoirs and thereby retain the adhesive therein. With reference to FIG. 10A, such a closure component can be disposed between each of the supporting layers and a respective adjunct material. The closure (or a cap) can be a removable component that is removed to allow the adhesive to flow from the reservoirs. As another variation, the closure component can be in a form of component that can be disposed in at least two different ways with respect to the reservoirs. In particular, the closure component can have openings that can align with the openings in the reservoirs.

However, before the adhesive is released from the reservoirs, the closure component can be disposed such that the openings therein are not aligned with the openings in the reservoirs and the closure is thus blocking the openings in the reservoirs and prevents release of the adhesive therefrom. The closure component can be, for example, slidable such that it can be moved to configuration in which its openings are aligned with the openings in the reservoirs. In some embodiments, the closure component can be in the form of a membrane or other thin member configured to rupture when pressure applied thereto exceeds a threshold.

The adjunct loading member 400 is configured such that it can be separated from the end effector 300 after the adjuncts 306, 316 are transferred to the jaws 302, 304 and are retained on the jaws using the adhesive. The adhesive can solidify and thus securely retain each adjunct on the jaw. In some embodiments, as discussed above, the adhesive can be allowed to solidify at a room temperature. Additionally or alternatively, it can be actively cooled using, e.g., a forced cool air.

The adhesive releasably retained in the reservoirs can be any suitable material. For example, it can be a flowable material such as polydioxanone (PDO), a high molecular weight poly(ethylene glycol) (PEG), or any other material. As mentioned above, the adhesive can be a pressure-sensitive adhesive.

Although in the illustrated embodiments heat is applied to an adhesive using an adjunct loading member, it should be appreciated that the heat can be applied in other manners. For example, in some implementations, an end effector can be configured to apply heat to the adhesive which can be releasably held in any type of an adhesive depot (e.g., a polymer layer having adhesive features, reservoirs in an adjunct loading member, etc.). The end effector can include a wire or other component that can be heated and can thus apply heat to the adhesive which thereby softens and can retain an adjunct on a jaw. In some embodiments, a separate heating component can be applied, which is not part of an end effector.

At least one adjunct can be applied to one or both jaws of the end effector during assembly of the end effector. For example, a jaw having a cartridge or both of the end effector's jaws can be pre-loaded with an adjunct during the assembly. In some cases, the jaw with the cartridge can be pre-loaded with an adjunct during the assembly, whereas an adjunct can be applied to the jaw having an anvil (e.g., using any of the adjunct loading members described herein) by a surgeon before or during a surgical procedure. Alternatively, as in the embodiments illustrated in FIGS. 10A and 10B, adjuncts can be applied to both jaws of the end effector by a surgeon (this however can be done during assembly as well).

Figure 11:
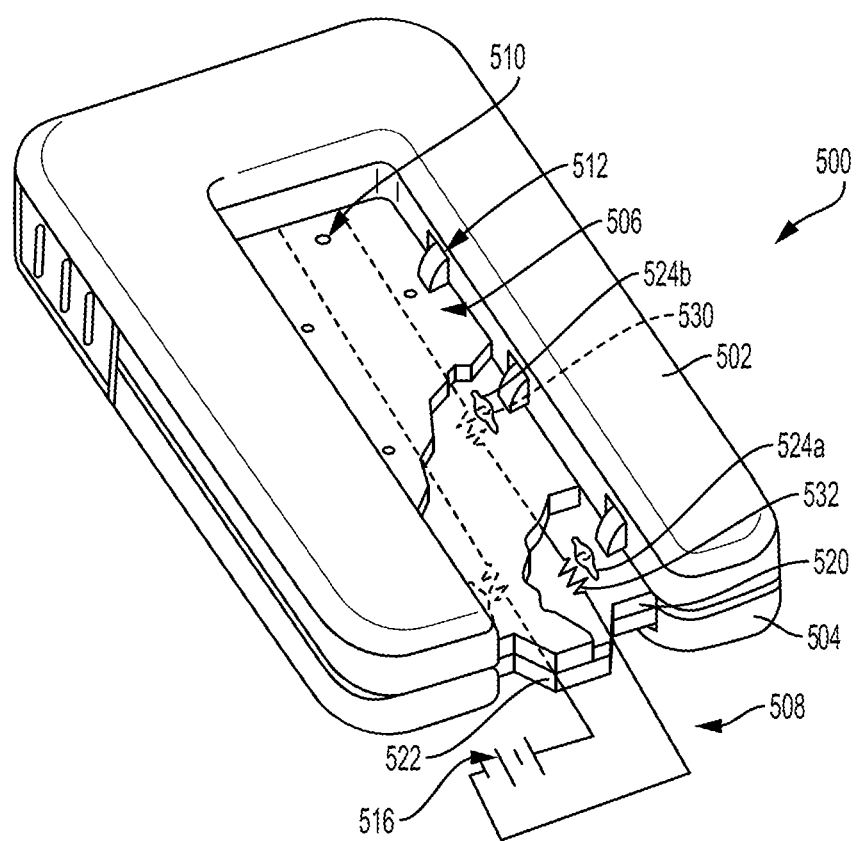
FIG. 11 is a perspective view of an adjunct loading member.

A configuration of an adjunct loading member can vary in different ways. FIG. 11 illustrates an example of an adjunct loading member 500 which can be similar to adjunct loading member 400 in FIGS. 10A and 10B. Thus, as shown in FIG. 11, the adjunct loading member 500 includes housings 502, 504 coupled to one another. The adjunct loading member 500 also includes supporting members 520, 522 disposed in the loading member 500 such that the housing 502, 504 enclose the supporting members 520, 522 along their perimeters. One side of the supporting members 520, 522 is not enclosed, as shown.

The supporting members 520, 522 have reservoirs releasably holding an adhesive, with one of the reservoirs, a reservoir 524a, shown formed in the supporting layer 520. A top of another reservoir 524b is also shown formed in the supporting member 520. One or both of the reservoirs and supporting members in which the reservoirs are formed can have openings that allow the adhesive stored in the reservoirs to be released therefrom. Thus, the reservoir 524b is shown to have an opening 530 above it, which can be formed in either the reservoir 524b itself or in the supporting member 520. Also, as discussed above, a closure component can be used (not shown), and an opening can be formed in this component as well.

FIG. 11 shows that the adjunct loading member 500 releasably retains therein an adjunct material 506, which is shown partially for illustration purposes. The adjunct material 506 includes openings 510 that are configured to receive the adhesive transitioning to the flowable state when the adhesive is released from a respective one of the reservoirs and through the opening to a jaw-facing surface of the respective adjunct material to thereby retain that adjunct material on the jaw. The adjunct material 506 is releasably retained on the supporting member 520. It should be appreciated that, although it is obscured in FIG. 11, the loading member 500 can include a second adjunct material releasably retained on the supporting member 522.

The adjunct material 306 is releasably retained in the adjunct loading member 500 using retainer elements 512, which can have any suitable configurations. Although the retainer elements 512 on one side of the adjunct material 306 are shown, it should be appreciated that they can also be formed on the opposed side of the adjunct material 306, in which case they are obscured in FIG. 11. Also, the retainer elements 512 can be configured such that they can be movable—e.g., when load is applied to the adjunct loading member 500, the retainer elements can be caused to move towards the edges of the housings 502, 504, such that the retainer elements release the adjunct material 306.

As shown in FIG. 11, a heating component 508 coupled to a power source 516 is disposed between the supporting members 520, 522. The heating component 508, e.g., its higher resistance portions 532 are used to apply heat to respective reservoirs to cause the adhesive stored in the reservoirs to transition from a non-flowable state to a flowable state.

Similar to the adjunct loading member 400 in FIGS. 10A and 10B, the adjunct loading member 500 is configured to have load applied thereto to cause it to release one or more adjunct materials therefrom which are transferred to jaw(s) of an end effector and are coupled to the jaw(s) using the adhesive.

In some embodiments, an adhesive depot can include an adhesive that is substantially liquid in a non-cured state and that is configured to be transitioned to an adhering, cured state in which it is at least partially non-liquid. This can involve curing the adhesive, which can be done using application of ultra violet (UV) light or infrared radiation. Additionally, load (or pressure) applied to the adhesive can facilitate curing the adhesive in some instances. In the cured, at least partially non-liquid state, the adhesive is used to couple an adjunct to a jaw of an end effector.

Figure 12A:
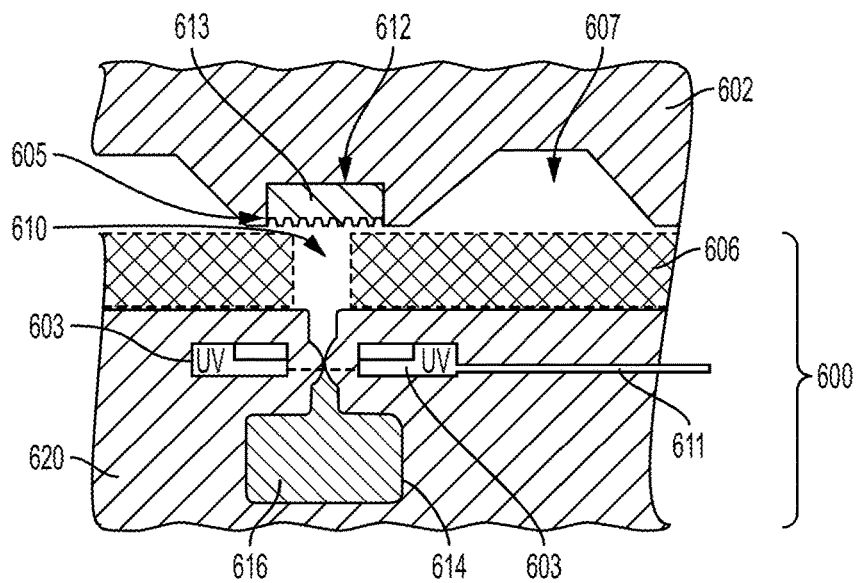
FIG. 12A is a cross-sectional view of a portion of an adjunct loading member configured to apply an adjunct material to a jaw of an end effector using a curable adhesive.
Figure 12B:
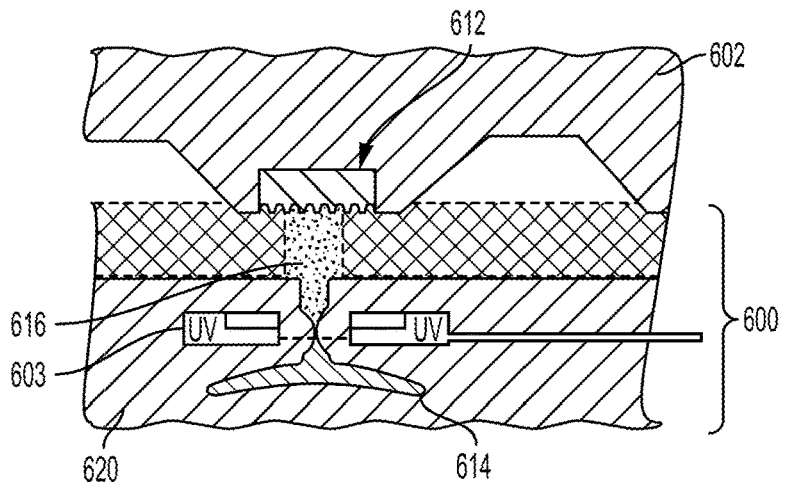
FIG. 12B is a cross-sectional view of the adjunct loading member of FIG. 12A, illustrating the adjunct loading member when load is applied thereto.
Figure 12C:
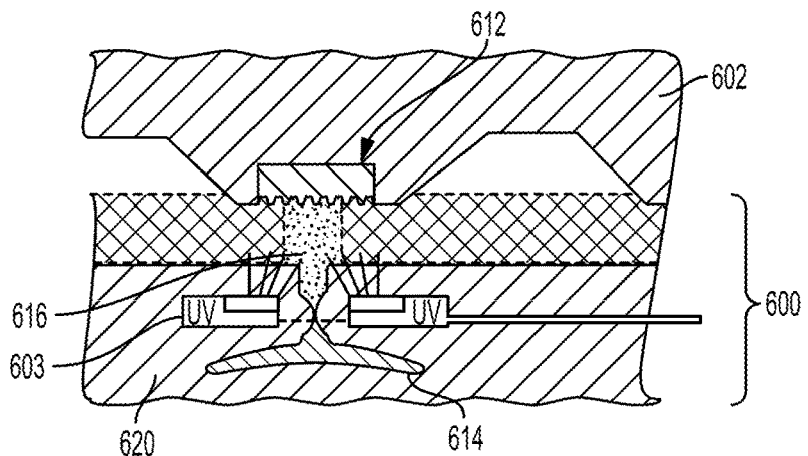
FIG. 12C is a cross-sectional view of the adjunct loading member of FIG. 12A, illustrating the adjunct loading member when load is applied thereto and the adhesive is being cured.

FIGS. 12A-12C illustrate an example of a portion of an adjunct loading member 600 including a supporting member 620 releasably retaining an adjunct material 606. The supporting member 620, which can be at least partially made from a silicone or other compressible material, includes one or more reservoirs holding an adhesive, one of which is shown as a reservoir 614 storing an adhesive 616. As shown in FIG. 12A, the reservoir 614 is disposed adjacent to an opening 610 in the adjunct material 606. The reservoir 614 can be an enclosed structure (e.g., formed from a suitable plastic) releasably holding the liquid adhesive 616. The adhesive 616 can be any suitable UV-curable adhesive, such as, for example, polyurethane, cyanoacrylate, or any other adhesive(s).

The adjunct material 606 is configured to be transferred to a jaw 602 of an end effector which is, in this example, a jaw having an anvil. The anvil 602 can have a tissue-facing surface 605 having staple-forming cavities or pockets 607. Also, as shown in FIGS. 12A-12C, the tissue-facing surface 605 has attachment portions, one of which is shown as an attachment portion 612 that is configured to receive the adhesive released from the reservoir 614. The attachment portions can be formed between the staple-forming pockets 607, though they can be formed in other areas of the tissue-facing surface 605. In some embodiments, as shown in this example, the attachment portion 612 can include an attachment feature 613 made from an elastomeric material (e.g., a pad) that is coupled to the tissue-facing surface 605. This feature can be patterned (e.g., knurled or otherwise roughened), which facilitates adherence of the adhesive to this portion. Also, the elastomeric material allows the attachment feature 613 to be deformed when the bond between the attachment portion 612 on the surface 605 and the adhesive coupled thereto (which retains an adjunct over the surface 605) is broken, as discussed in more detail in the example shown in FIGS. 15A-15C below.

As shown, the adjunct loading member 600 also includes UV light applicators 603 configured to apply UV light to the adhesive as it is released from the adhesive reservoirs. The UV light applicators 603 are coupled to a cable 611 (e.g., a fiber optic cable) that couples the applicators to a UV light source. Also, in some embodiments, the UV light applicators 603 can be associated with UV-emitting light emitting diodes (LEDs).

FIG. 12A illustrates the adjunct loading member 600 before load is applied thereto. When the load so applied to the adjunct loading member 600 (e.g., using the jaws of the end effector, manually, etc.), the reservoir 614 is deformed, broken, or its configuration is otherwise changed such that the adhesive 616 is transferred from the reservoir 614, through the opening 610 in the adjunct 606, and onto the surface of the jaw 302, as shown in FIG. 12B. The adhesive 616 is transferred to the tissue-facing surface 605 of the jaw 302 so as to be disposed on the surface of the attachment portion 612. As the adhesive 616 is being released, the UV light applicators 603 are activated to apply UV light to the adhesive 616 to cause it to cure, as illustrated in FIG. 12C. In this way, the adhesive 616 is deposited on the surface of the jaw in the adhering, non-cured state (or only partially cured) in which it is then cured and thus attaches the adjunct 606 to the jaw 602. The adjunct loading member 600 can then be separated from the end effector.

It should be appreciated that the portion of the adjunct loading member 600 is shown in FIGS. 12A-12C by way of example only. Also, the adjunct loading member 600 can include multiple reservoirs with the adhesive, more than one openings can be formed in the adjunct, as well as other variations are possible.

Figure 13A:
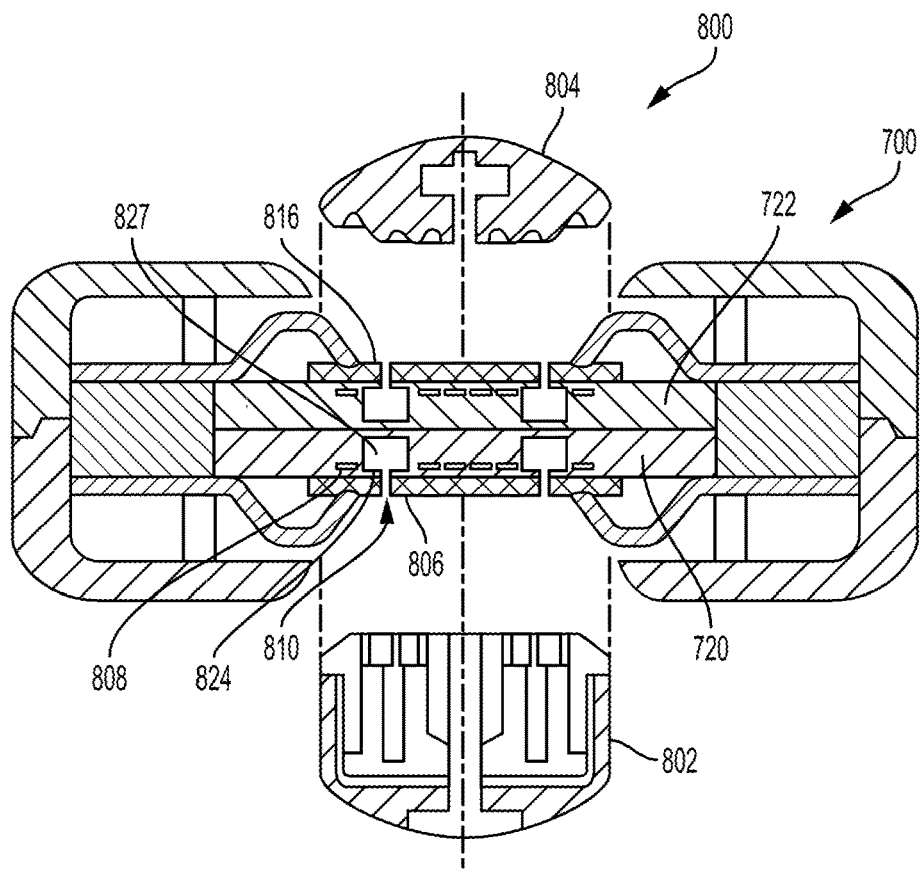
FIG. 13A is a cross-sectional view of a portion of an adjunct loading member configured to apply an adjunct material to first and second jaws of an end effector using a curable adhesive.
Figure 13B:
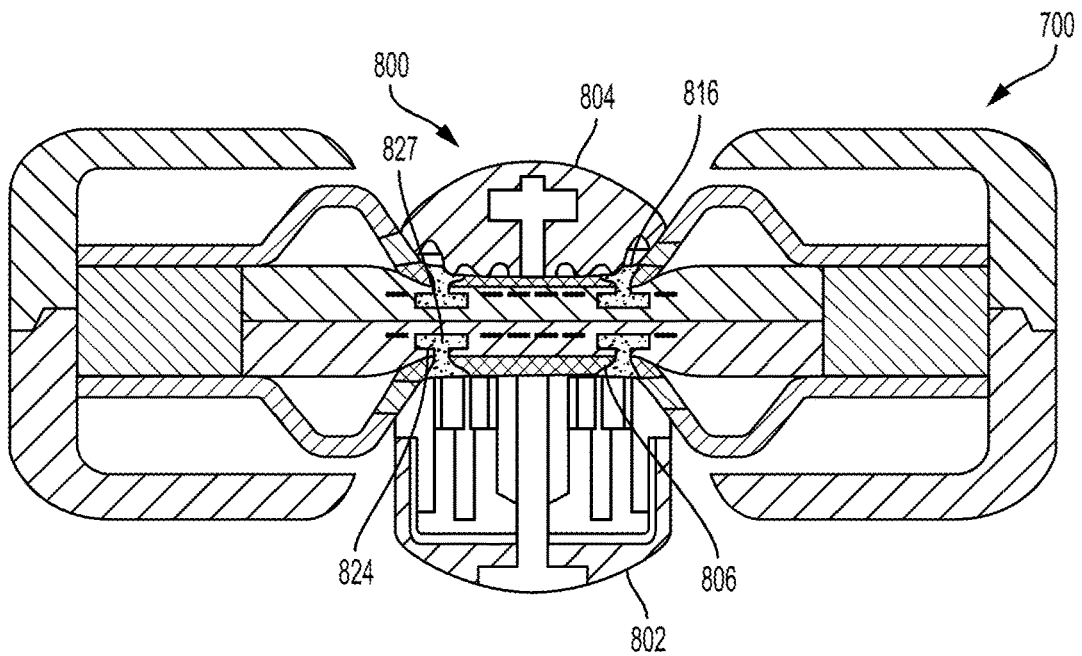
FIG. 13B is a cross-sectional view of the adjunct loading member of FIG. 13A, illustrating the adjunct loading member when load is applied thereto.

FIGS. 13A and 13B illustrate another example of an adjunct loading member 700 configured to releasably hold first and second adjunct materials 806, 816 and to apply these adjunct materials to first and second jaws 802, 804 of an end effector 800. Similar to adjunct loading member 600 in FIGS. 12A-12C, a substantially liquid adhesive released from the adjunct loading member 700 is configured to be cured using UV light, heat, or in other manner. As shown in FIGS. 13A and 13B, the adjunct loading member 700 is similar to adjunct loading member 400 shown in FIGS. 10A and 10B, and therefore a detailed description is not repeated. However, as mentioned above, the adjunct loading member 700, releasably stores in reservoirs formed in first and second supporting members 720, 722 an adhesive that is cured upon it is release from the reservoirs such that it is used to retain the adjuncts on the jaw in its cured state.

Describing by way of example one of the reservoirs included in the adjunct loading member 700, a reservoir 824 in the supporting member 720 is configured to provide an adhesive 827 stored therein when load is applied to the adjunct loading member 700 as shown in FIG. 13B. A UV light applicator 808 or other (e.g., infrared radiation) applicator is configured to apply UV or other radiation to the adhesive 827 as it is released from the reservoir 824. In this way, the adhesive is used to retain the adjunct on the jaw as the adjunct is transferred to the jaw.

Figure 14:
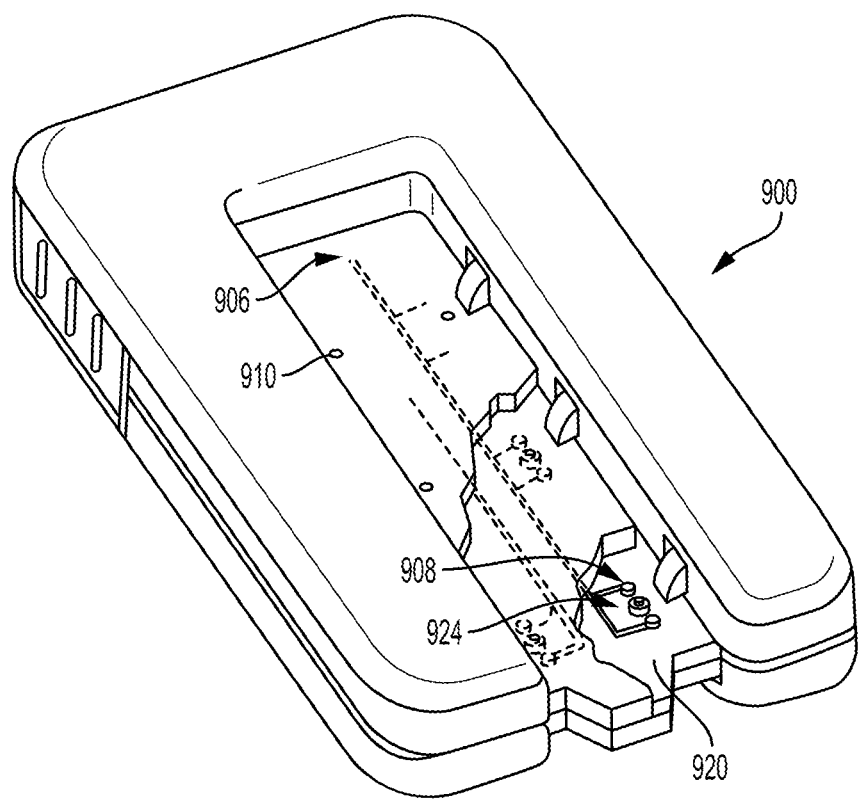
FIG. 14 is a perspective view of an adjunct loading member.

Any suitable component can be used to apply radiation to an adhesive to cause it to transition from a state in which it is not cured to an adhering state in which it is cured. FIG. 14 illustrates one embodiment of an adjunct loading member 900 that can be used to apply radiation to an adjunct material 906. The adjunct loading member 900 can be generally similar to adjunct loading member 500 in FIG. 11 and is therefore not described in detail. In this example, an adhesive stored in a reservoir, such as a reservoir 924 formed in a supporting member 920 is configured to be cured when it is released from the reservoir 924 when load is applied to the adjunct loading member 900 and the adhesive is cured using radiation emitted from a UV applicator 908. Other types of radiation, however, can be used additionally or alternatively. Similar to the manner described above in connection with the adjunct loading member 500 (FIG. 11), the adhesive can be released from the reservoir and caused to flow through an adjacent opening 510 formed in the adjunct 906. Although not shown in FIG. 14, the adjunct loading member 900 can also have a second adjunct material releasably retained therein and configured to be transferred therefrom and attached to a second jaw of an end effector similar to the adjunct 906.

Figure 15A:
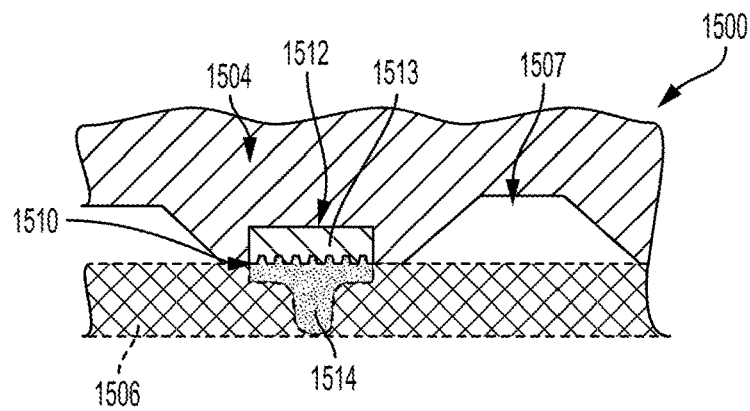
FIG. 15A is a cross-sectional view of a portion of an adjunct material releasably coupled to a first jaw of an end effector using an adhesive.

Regardless of the specific way in which an adjunct material is coupled to a jaw of an end effector, it is required to properly separate the adjunct material from the jaw when the adjunct is applied to tissue. It is desired to release the adjunct from the jaw in an efficient manner. This can be achieved, for example, by fracturing the adhesive that attaches the adjunct to the end effector. FIG. 15A illustrates an example of a portion of an adjunct material 1506 attached to the jaw 1504 of an end effector 1500 by an adhesive 1514, which can be cured in a desirable manner (e.g., using a UV light applied via a loader, or in other manners). The adhesive 1514 releasably attaches the adjunct material 1506 to the jaw 1504 by being at least partially disposed in an opening 1510 formed in the adjunct material 1506.

Similar to adhesive 616 in FIGS. 12A-12C, the adhesive 1514 in FIG. 15A is coupled to the jaw 1504 at an attachment region or portion 1512 on the surface of the jaw 1504. Similar to attachment portion 612 in FIGS. 12A-12C, the attachment portion 1512 can have a deformable attachment feature 1513 that is patterned to facilitate coupling the adhesive thereto. The attachment feature 1513 can be formed from an elastomeric material such that it can deform when a force is applied thereto.

Figure 15B:
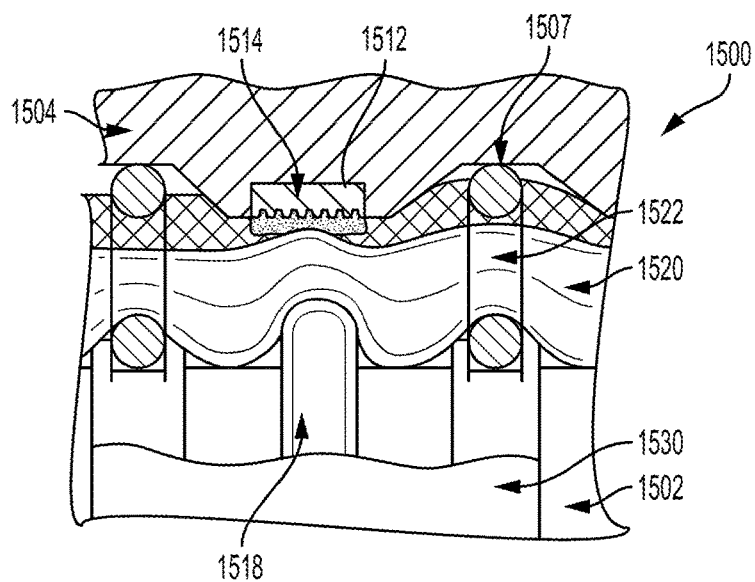
FIG. 15B is a cross-sectional view of the adjunct material of FIG. 15A, illustrating staples fired from a second jaw of the end effector and the end effector causing the adhesive to break.

The end effector 1500 can be configured to cause the adjunct material 1506 to separate from the jaw 1504 when staples are fired from a jaw 1502 having a cartridge that is shown schematically in FIG. 15B. For example, as shown, the jaws 1502, 1504 are approximated to clamp tissue 1520 therebetween and a stapler driver 1530 movably seated in the jaw 1502 causes staples 1522 to fire from staple holding cavities in the jaw 1502 so as to penetrate the tissue 1520 and the adjunct 1506. The staples 1522 are urged into corresponding staple-forming cavities or pockets 1507 formed on the surface of the jaw 1504 such that the staples 1522 are closed and attach the adjunct 1506 to the tissue 1520.

In the example illustrated, the stapler driver 1530 includes protruding members 1518 configured to push the cured adhesive 1514 towards the attachment portion 1512 and into the attachment feature 1513 (which can deform to some degree) when the staples 1522 are fired. This can cause the adhesive 1514 to break, fracture, deform, or otherwise change its configuration. In some instances the cured adhesive 1514 can be brittle and applying load thereto causes it to fracture, crack, or break.

Figure 15C:
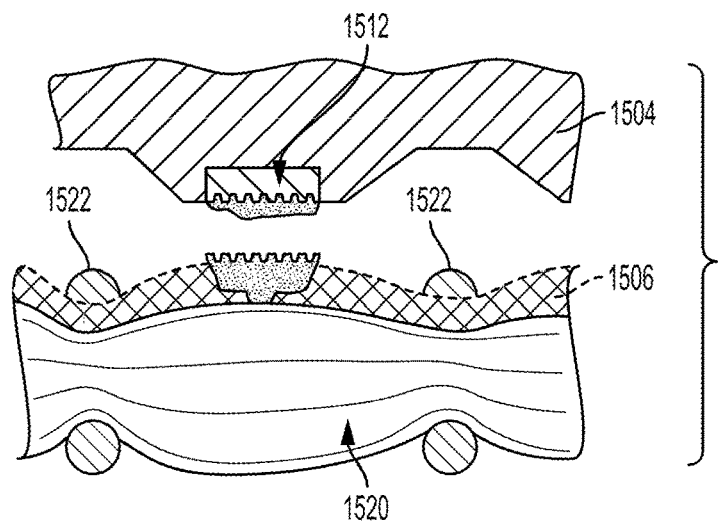
FIG. 15C is a cross-sectional view of the adjunct material of FIG. 15A, illustrating the adjunct material separated from the end effector.

It should be appreciated that only portions of the adjunct 1506 and the end effector 1500 are shown in FIGS. 15A-15C and that multiple attachment portions similar to the attachment portion 1512 (or having other configurations) can be formed on the jaw 1504 and are used to couple the adjunct 1506 to the jaw 1504 using the adhesive 1514. Accordingly, multiple corresponding protruding members on the stapler driver 1530 can cause the adhesive at the corresponding attachment portions to break. In this way, the adjunct 1502 can be decoupled from the attachment region 1512 and thereby be released from the jaw 1504. Thus, FIG. 15C illustrates the tissue 1520 and the adjunct 1506 stapled together by the staples 1522 and decoupled from the jaw

1504 and thus from the end effector 1500. A portion of the adhesive 1514, which can be a biodegradable and/or bioabsorbable material, can remain with the adjunct 1506, as shown.

It should be appreciated that the described adjunct materials and systems and methods used to apply the adjunct materials to at least one jaw of an end effector can have various configurations. For example, although, as discussed above, the adjunct materials can have openings formed therein that allow an adhesive from an adhesive despot to be applied to the surface of the adjunct, in some embodiments, the openings may not be formed. In such embodiments, the adhesive can be flowed from an adhesive depot (e.g., one or more reservoirs) through pores, spaces between fabric strands, or other structures in the adjunct material. For example, the adjunct material can be porous and the adhesive are flow therethrough to a surface of the jaw. The pores can be formed at any suitable ways, and, in some instances, they can be larger at predetermined locations through which the adhesive can flow easier.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A loading system comprising: at least one adjunct material configured to be transferred from an adjunct loading member to one of a first and a second jaw of an end effector, the first and second jaws being configured to clamp tissue therebetween; a polymer layer coupled to a jaw-facing surface of the at least one adjunct material; a supporting member configured to releasably retain the at least one adjunct material; and an adhesive depot having an adhesive configured to transition from a non-flowable state to a flowable state upon an application of heat, when the at least one adjunct material is released from the adjunct loading member and transferred to the one of the first and the second jaw, to retain the at least one adjunct material on the one of the first and the second jaw, wherein the adhesive depot comprises a plurality of individual protrusions formed on a surface of the polymer layer facing one of the first and second jaw and comprising the adhesive.

2. The adjunct loading system of claim 1, wherein the at least one adjunct material is released from the adjunct loading member and transferred to one of the one of the first and the second jaws under application of load to the adjunct loading member.

3. The adjunct loading system of claim 2, wherein the load is applied to the adjunct loading member by the first and second jaws configured to clamp the adjunct loading member therebetween.

4. The adjunct loading system of claim 1, wherein the at least one adjunct material is coupled to the polymer layer.

5. The adjunct loading system of claim 1, wherein the at least one protrusion is formed at a location on the polymer layer corresponding to a location of an attachment feature formed on the one of the first and the second jaw, the adhesive being configured to be disposed on the attachment feature.

6. The adjunct loading system of claim 5, wherein the attachment feature comprises a roughness pattern.

7. The adjunct loading system of claim 1, comprising at least one source of heat.

8. A loading system comprising: at least one adjunct material configured to be transferred from an adjunct loading member to one of a first and a second jaw of an end effector and comprising a plurality of openings, the first and second jaws being configured to clamp tissue therebetween; a supporting member configured to releasably retain the at least one adjunct material; and an adhesive depot having an adhesive configured to transition from a non-flowable state to a flowable state upon an application of heat, when the at least one adjunct material is released from the adjunct loading member and transferred to the one of the first and the second jaw, to retain the at least one adjunct material on the one of the first and the second jaw, wherein the adhesive depot comprises a plurality of reservoirs formed in the supporting member and each releasably holding the adhesive, wherein the adhesive is configured to flow via one or more openings of the plurality of openings.

9. The adjunct loading system of claim 8, wherein the adhesive is held in the plurality of reservoirs in the non-flowable state in which the adhesive is substantially non-liquid such that the adhesive can transition under the application of at least one of heat and force to the flowable state in which the adhesive is at least partially, liquid.

10. The adjunct loading system of claim 8, wherein the adhesive is held in the plurality of reservoirs in the non-flowable state in which the adhesive is substantially liquid such that the adhesive can transition under the application of at least one of heat and force to the flowable state in which the adhesive is at least partially non-liquid.

11. The adjunct loading system of claim 8, wherein the plurality of openings being configured to receive the adhesive transitioning to the flowable state when the adhesive material is released from a respective one of the plurality of reservoirs and through the opening to a jaw-facing surface of the at least one adjunct material to thereby retain the at least one adjunct material on the one of the first and the second jaw.

12. The adjunct loading system of claim 11, wherein the adhesive is caused to transition to the flowable state and is released from a respective one of the plurality of reservoirs under at least one of application of heat and application of load.

* * * * *